US00PP30224P3

(12) United States Plant Patent
Suphachadiwong

(10) Patent No.: US PP30,224 P3
(45) Date of Patent: Feb. 19, 2019

(54) ***SANSEVIERIA* PLANT NAMED 'SUPSAN1608'**

(50) Latin Name: *Sansevieria cylindrica*
Varietal Denomination: SUPSAN1608

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/732,575

(22) Filed: Nov. 29, 2017

(65) Prior Publication Data

US 2018/0153082 P1 May 31, 2018

(30) Foreign Application Priority Data

Nov. 30, 2016 (QZ) ..... PBR 2016/3007

(51) Int. Cl.
*A01H 5/12* (2018.01)

(52) U.S. Cl.
USPC ..... Plt./382
CPC ..... *A01H 5/12* (2013.01)

(58) Field of Classification Search
USPC ..... Plt./382
See application file for complete search history.

*Primary Examiner* — Susan McCormick Ewoldt
(74) *Attorney, Agent, or Firm* — Samuel R. McCoy, Jr.

(57) ABSTRACT

A new and distinct *Sansevieria* plant named 'SUPSAN1608' which is characterized by the combination of a compact growth habit, broad orbicular plant form, thick succulent foliage with a narrow ovate to lanceolate shape, yellow-green foliage with a silver hue and prominent green mottled radial bands, and the stability of all characteristics from generation to generation.

2 Drawing Sheets

Latin name of the genus and species: The Latin name of the genus and species of the novel variety disclosed herein is *Sansevieria cylindrica.*

Variety denomination: The inventive variety of *Sansevieria* disclosed herein has been given the variety denomination 'SUPSAN1608'.

CROSS REFERENCE TO RELATED APPLICATIONS

This application claims priority to the Community Plant Variety Rights application number 2016/3007, filed Nov. 30, 2016, which is herein incorporated by reference.

BACKGROUND OF THE INVENTION

Parentage: The *Sansevieria* variety 'SUPSAN1608' originated as a seedling selection from the controlled pollination of the proprietary seed parent, *Sansevieria cylindrica* 'MXJRM0061' (not patented), with the proprietary pollen parent, *Sansevieria cylindrica* 'MXU1806H61' (not patented). Both parents were developed by, and are owned by, the inventor and were never commercially released. Said crossing was conducted by the inventor in a small, netted greenhouse in Chonburi, Thailand in December of 2011. Seeds from said cross were harvested, then germinated, and the resulting seedlings were grown to a mature size in order to evaluate for a desirable combination of commercial characteristics. In August of 2013, one candidate plant was observed to exhibit a unique growth habit and leaf coloration. After confirmation of the distinctness and stability of the characteristics first observed, the inventor selected the new *Sansevieria* cultivar, 'SUPSAN1608', for commercial introduction.

Asexual Reproduction: Asexual reproduction of 'SUPSAN1608' by way of harvesting vegetative ground shoots was first initiated in August of 2013 at Chonburi, Thailand. Access to all plants was restricted, as plants were kept in a greenhouse not open to the public. Through subsequent propagation of vegetative ground shoots, five generations have been reproduced which have shown that the unique features of this cultivar are stable and reproduced true to type.

SUMMARY OF THE INVENTION

The cultivar 'SUPSAN1608' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'SUPSAN1608'. These characteristics in combination distinguish 'SUPSAN1608' as a new and distinct *Sansevieria* cultivar:

1. *Sansevieria* 'SUPSAN1608' exhibits a compact, equitant, and upright to outward growth habit; and
2. *Sansevieria* 'SUPSAN1608' exhibits a vertically flattened, broad orbicular plant form; and
3. *Sansevieria* 'SUPSAN1608' exhibits thick, succulent foliage with a narrow ovate to lanceolate shape and terete cross-section; and
4. *Sansevieria* 'SUPSAN1608' exhibits yellow-green foliage with a silver hue and prominent green mottled radial bands.

BOTANICAL DESCRIPTION OF THE PLANT

Figure 1:
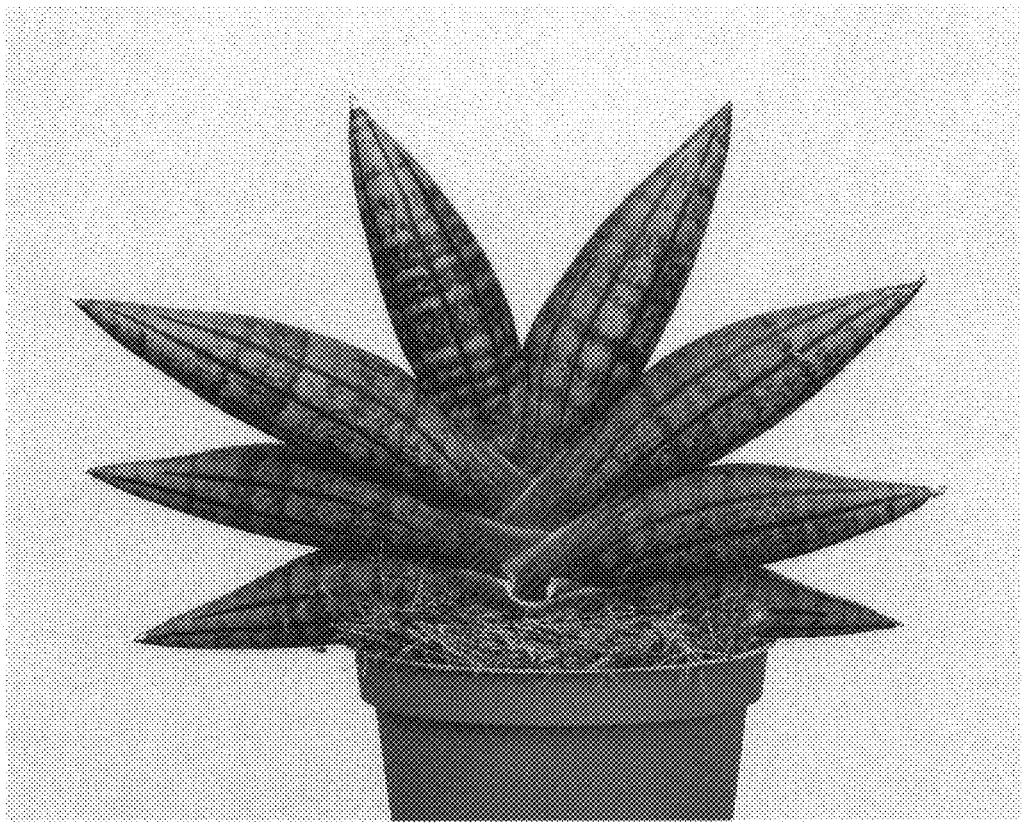
FIG. 1 illustrates, as nearly true as it is reasonably possible to make the same in color photographs of this type, an exemplary plant of 'SUPSAN1608' grown in a commercial greenhouse in Chonburi, Thailand. This plant is approximately 12 months old, shown planted in an 8 cm container.
Figure 2:
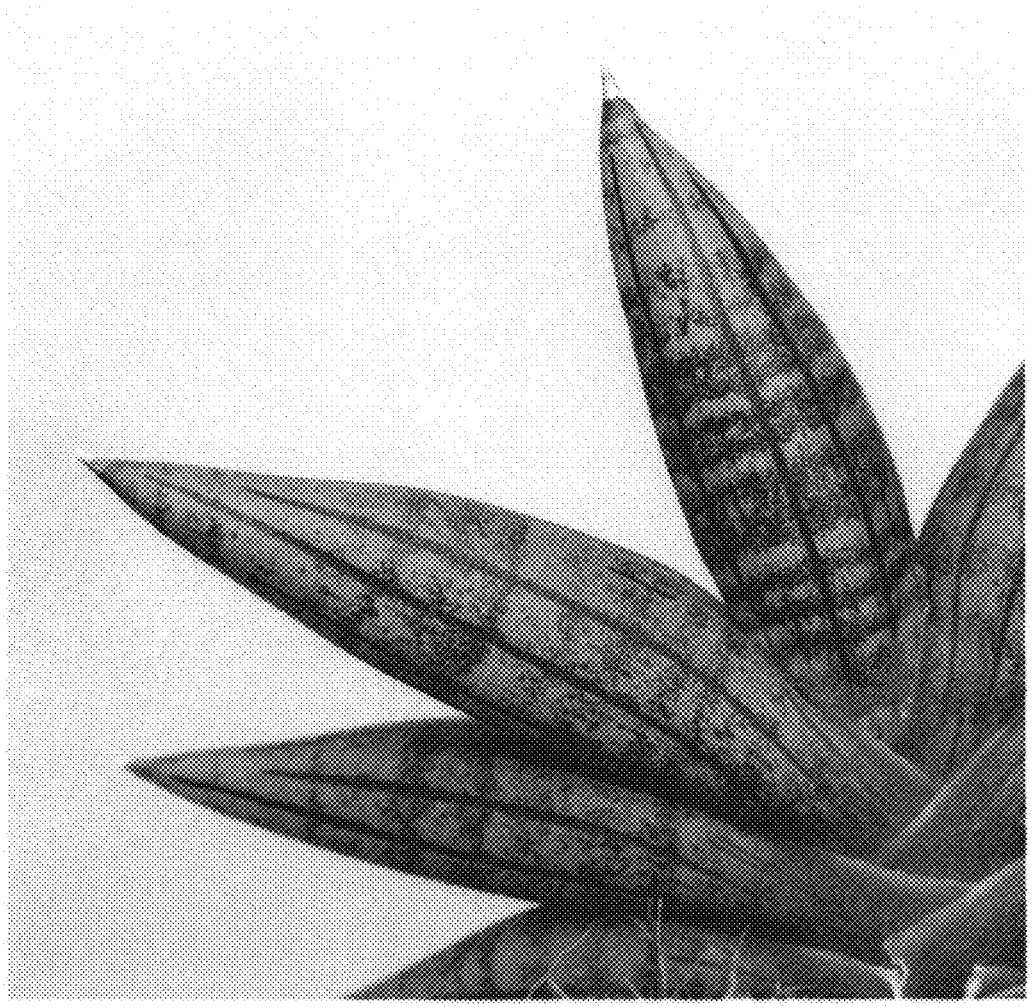
FIG. 2 illustrates, as nearly true as it is reasonably possible to make the same in color photographs of this type, the typical foliage of 'SUPSAN1608'.

The following observations and measurements, made in October of 2017, describe averages from a sample set of six specimens of 12 month old 'SUPSAN1608' plants grown in 8 cm containers, at a commercial greenhouse in Chonburi, Thailand. The plants were grown using conventional greenhouse production protocols for *Sansevieria* plants which consisted of overhead irrigation, 50% shade cloth, and no fertilizer. No photoperiodic or chemical treatments were given to the plants.

Those skilled in the art will appreciate that certain characteristics will vary with older or, conversely, with younger plants. 'SUPSAN1608' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SUPSAN1608' and comparisons with the parents and most similar commercial variety of *Sansevieria* are provided below.

Plant description:

*Growth habit*.—Monopodial perennial; equitant and upright to outward.

*Plant form*.—Vertically flattened, fan-shaped; broad orbicular.

*Average height*.—10.0 cm.

*Plant spread*.—3.4 cm at the narrowest point, and 15.5 cm at the widest point.

*Plant vigor*.—Low.

*Growth rate*.—Moderate.

*Propagation type*.—Division of vegetative ground shoots; harvesting ground shoots from the mother plant.

*Propagation details*.—The time needed to root a shoot division is approximately 2 to 3 months with temperatures ranging from approximately 17 to 40 degrees Celsius.

*Disease resistance*.—Plants have not been observed to be susceptible or resistant to pathogens and pests common to *Sansevieria*.

*Environmental tolerances*.—Adapt to, at least, USDA Zones 10 and 12 and temperatures as high as 40 degrees Celsius; moderate tolerance to rain; moderate to high tolerance to wind.

Root system:

*General*.—Moderately dense and moderately branched rooting; roots are slightly fibrous.

*Distribution in the soil profile*.—Shallow to moderately deep.

*Diameter of roots*.—0.15 cm on average.

*Texture*.—Smooth; no root hairs.

*Color*.—Greyed-yellow, nearest to in between RHS 161B and 161C.

Stem:

*Branching habit*.—Monopodial, equitant; decurrent leaf bases form the stem.

*Number of primary (main) stems per plant*.—One.

*Number of secondary (lateral) branches per plant*.—None.

*Appearance and shape*.—Stem is not visible; decurrent leaf bases form the stem.

*Length*.—The decurrent leaf bases collectively have an average length of 4.2 cm.

*Diameter*.—The decurrent leaf bases collectively have an average diameter of 1.8 cm.

*Internode length*.—0.5 cm.

Foliage:

*Arrangement*.—Distichous.

*Attachment*.—Decurrent.

*Division*.—Simple.

*Quantity*.—9.

*Attitude*.—Outward; at an average angle of 70 degrees to vertical.

*Lamina*.—Dimensions — 8.5 cm long and 1.8 cm wide. Thickness — Approximately 1.8 cm. Shape of blade — Narrow ovate to lanceolate; succulent. Cross-section — Terete. Aspect — Nearly straight. Apex — Acute with a slightly papery tip on older leaves, which is colored greyed-white, nearest to RHS 156D. Base — Decurrent. Margin — Leaves are terete so there are no margins, with the exception of the leaf base; leaf base margins are entire. Texture of upper surface — Glabrous, smooth, and succulent. Texture of lower surface — Glabrous, smooth, and succulent. Luster of the upper surface — Matte. Luster of the lower surface — Matte. Color — Juvenile foliage, upper surface — Green, nearest to RHS 138C, with mottled radial bands colored green, nearest to RHS 139A. Juvenile foliage, lower surface — Green, nearest to RHS 138C, with mottled radial bands colored green, nearest to RHS 139A; the base is green, nearest to RHS 143C. Mature foliage, upper surface — Yellow-green, nearest to RHS 146B, with mottled radial bands colored green, nearest to RHS 139A. Mature foliage, lower surface — Yellow-green, nearest to RHS 147D, with mottled radial bands colored green, nearest to RHS 139A; the base is green, nearest to in between RHS 137A and 137B; margins of the decurrent base are a translucent yellow-green, nearest to RHS 147D. Venation — Pattern — Parallel. Color, upper surface — Green, nearest to RHS N189A. Color, lower surface — Green, nearest to RHS N189A.

*Petiole*.—No petioles present, leaves are decurrent.

Inflorescence: No flowering has been observed to date.

Comparisons with the Parent Plants

Plants of the new cultivar 'SUPSAN1608' differ from the seed parent, *Sansevieria cylindrica* 'MXJRM0061' (not patented), by the characteristics described in Table 1.

TABLE 1

| Characteristic | 'SUPSAN1608' | 'MXJRM0061' |
|---|---|---|
| Growth habit. | More compact than 'MXJRM0061'. | Less compact than 'SUPSAN1608'. |
| Foliage length. | Shorter than 'MXJRM0061'. | Longer than 'SUPSAN1608'. |
| Foliage; apex. | More acute than 'MXJRM0061'. | Less acute than 'SUPSAN1608'. |
| General coloration of the foliage. | Darker yellow-green. | Lighter yellow-green. |
| Prominence of the color pattern on the foliage. | More prominent green mottled radial bands. | Less prominent green mottled radial bands. |

Plants of the new cultivar 'SUPSAN1608' differ from the pollen parent, *Sansevieria cylindrica* 'MXU1806H61' (not patented), by the characteristics described in Table 2.

TABLE 2

| Characteristic | 'SUPSAN1608' | 'MXU1806H61' |
|---|---|---|
| Growth habit. | More compact than 'MXU1806H61'. | Less compact than 'SUPSAN1608'. |
| Rate of growth. | Slower growing than 'MXU1806H61'. | Faster growing than 'SUPSAN1608'. |
| Leaf length. | Shorter than 'MXU1806H61'. | Longer than 'SUPSAN1608'. |
| General coloration of the foliage pattern. | Darker green mottled radial . bands | Lighter green mottle dradial bands. |

Comparison with the Most Similar Sansevieria Cultivar Known to the Inventor

Plants of the new cultivar 'SUPSAN1608' are most similar to the commercial cultivar, *Sansevieria cylindrica* 'SAN201202' (U.S. Plant Pat. No. 24,457). A comparison of 'SUPSAN1608' with 'SAN201202' is described in Table 3.

TABLE 3

| Characteristic | 'SUPSAN1608' | 'SAN201202' |
|---|---|---|
| Growth habit. | More compact than 'SAN201202'. | Less compact than 'SUPSAN1608'. |
| Plant form. | Less flattened. | More flattened. |
| Foliage shape. | Narrow ovate to lanceolate; terete. | Linear; terete. |
| Foliage dimensions. | Shorter and broader than 'SAN201202'. | Longer and narrower than 'SUPSAN1608'. |
| Foliage thickness. | Thicker than 'SAN201202'. | Thinner than 'SUPSAN1608'. |
| General coloration of the foliage. | Yellow-green with a silver hue. | Dark green with a silver hue. |
| Prominence of leaf venation. | More prominent. | Less prominent. |
| Prominence of the color pattern on the foliage. | More prominent green mottled radial bands. | Less prominent green mottled radial bands. |

That which is claimed is:

1. A new and distinct variety of *Sansevieria* plant named 'SUPSAN1608', substantially as described and illustrated herein.

* * * * *